United States Patent
Shoher et al.

(10) Patent No.: US 6,403,212 B1
(45) Date of Patent: *Jun. 11, 2002

(54) MOLDABLE DENTAL MATERIAL COMPOSITION

(76) Inventors: Itzhak Shoher, 50 Shlomo Hamelech St., Tel Aviv (IL), 64386; Aharon Eliyahu Whiteman, J. L. Peretz St. 13, Petach Tikvah (IL), 49206

( * ) Notice: Subject to any disclaimer, the term of this patent is extended or adjusted under 35 U.S.C. 154(b) by 0 days.

This patent is subject to a terminal disclaimer.

(21) Appl. No.: 08/279,907

(22) Filed: Jul. 25, 1994

Related U.S. Application Data

(63) Continuation-in-part of application No. 08/005,595, filed on Jan. 19, 1993, now Pat. No. 5,332,622.

(51) Int. Cl.$^7$ ................................................. B32B 5/16
(52) U.S. Cl. ........................ 428/323; 428/328; 428/212; 428/304.4; 428/307.3; 428/457; 428/613; 433/223; 433/228.1; 419/2; 29/896.1; 75/955
(58) Field of Search ................................. 428/212, 323, 428/328, 457, 613, 304.4, 307.3; 433/223, 228.1; 419/2; 29/160.6, 896.1; 75/955

(56) References Cited

U.S. PATENT DOCUMENTS 4,997,699 A * 3/1991 Shoher et al. .............. 428/212
5,272,184 A * 12/1993 Shoher et al. .............. 523/118
5,332,622 A * 7/1994 Shoher et al. .............. 428/323

* cited by examiner

*Primary Examiner*—Marie Yamnitzky

(57) ABSTRACT

A moldable dental material composition comprising high-fusing temperature metal particles, a volatile binder, preferably in a concentration of above at least twenty percent (20%) of the material composition, and finely divided carbonaceous particles, preferably of activated carbon. The high-fusing temperature metal particles should have an irregular, nonspherical geometry and a thin cross-sectional average thickness. The moldable dental composition may also contain low-fusing temperature metal particles for enhanced wetting of the high-fusing metal particles during heat treatment at a heat-treatment temperature which will melt the binder and substantially melt the low-fusing metal particles, if present. Heat treatment forms a porous metal structure having a capillary network of voids and a high void volume.

11 Claims, No Drawings

MOLDABLE DENTAL MATERIAL COMPOSITION

FIELD OF THE INVENTION

This invention is a continuation-in-part of U.S. patent application Ser. No. 08/005,595, filed Jan. 19, 1993, now U.S. Pat. No. 5,332,622, and relates to an improved moldable dental material composition and method for forming and/or repairing dental restorations.

BACKGROUND OF THE INVENTION

In crown and bridge prosthodontics, metal copings are conventionally used to provide the essential structural strength and rigidity necessary for a dental restoration to resist the forces of mastication. In a ceramic-to-metal dental restoration, the metal coping forms the understructure, over which is applied a fired-on coating of porcelain or acrylic. A coating of porcelain is used over the coping for aesthetics and to simulate natural teeth. To the dental patient, color and the overall appearance of the dental restoration are critical factors in the satisfaction of the restoration. Accordingly, the color of the metal coping is important and should enhance the aesthetics of the restoration. For a ceramic-to-metal dental restoration, the metal coping should enhance the porcelain by providing a background color contrast.

In a co-pending application of Applicants entitled Moldable Dental Material and Method, Ser. No. 887,245, filed May 19, 1992, now U.S. Pat. No. 5,234,343, a dental material composition is taught which can be readily shaped or molded into any desired shape for repairing and/or forming a dental restoration, without waxing and casting. The composition of the material and method of application is taught in Applicants' U.S. Pat. Nos. 4,742,861 and 4,990,394, the disclosure of which is herein incorporated by reference. In general, the dental material is composed of high- and low-fusing temperature metal particles combined in a matrix with a volatile binder for forming a dental restoration directly on a refractory die or model of the tooth or teeth to be restored. The material is shaped on the die into a desired configuration and heat-treated at a temperature to melt, or substantially melt, the low-fusing temperature metal particles and to volatize the binder, resulting in a porous, sponge-like structure having the shape it was given prior to heat treatment. A low-melting temperature filler material, preferably of gold, is then melted into the sponge-like structure to form a solid metal coping, with a configuration identical to the configuration of the shaped material on the refractory die before heat treatment and without experiencing distortion and/or shrinkage.

The solidified metal should possess a desirable color, which is reproducible with high accuracy, for use in forming a dental restoration. Heretofore, the process was temperature sensitive and even minor variations in the temperature during the heat-treatment procedures would permit some oxidation of the metals to occur, which could deleteriously affect its color, and even more seriously, could inhibit the flow of filler material into the porous sponge, which would affect the size of the solidified sponge. In fact, even the type of furnace used or its condition was able to affect the ability to accurately control the temperature during the heat-treatment procedures. Although sophisticated furnace temperature control equipment is commercially available, the implementation of such equipment is costly and would be unacceptable to the dental practitioner. The sensitivity to temperature variation also limited the process to the fabrication within the furnace of one restoration at a time.

SUMMARY OF THE INVENTION

A dental material composition has been discovered which can be molded with little effort to form a dental coping, dental crown, or filling. The composition preferably containing wax forms a material which may be worked on a refractory die, dies made of other materials or in the mouth. The procedure for forming a metal coping, repairing a dental restoration or filling a tooth can be readily practiced either at the dental laboratory or by the dentist in the dental office.

The moldable dental composition of the present invention comprises: high-fusing temperature metal particles having an irregular nonspherical geometry and a thin cross-sectional average thickness, a volatile binder preferably comprising wax, and finely divided carbonaceous particles in a concentration above at least 0.005 wt. % of the dental material. The composition may also contain low-fusing metal particles having a melting temperature below a preselected heat-treatment temperature sufficient to melt the binder and the low-fusing metal particles, but not the high-fusing metal particles.

The moldable dental material of the present invention comprises:

high-fusing temperature metal particles having an irregular, nonspherical geometry and a thin cross-sectional average thickness;

a volatile binder in a concentration of at least twenty percent (20%) by volume; and finely divided carbonaceous particles, in a concentration above at least 0.005 wt.% of the dental composition.

DETAILED DESCRIPTION OF THE INVENTION

The dental material of the present invention is a moldable composition of metal particles formed, preferably, from a mixture of high- and low-fusing temperature metal particles and a volatile binder.

Upon heat treatment, the binder should vaporize to leave a porous, sponge-like structure having a capillary network of multiple voids uniformly distributed throughout the structure, with a void volume preferably of at least twenty percent (20%), and up to eighty percent (80%).

The binder may be any suitable vehicle which will vaporize upon heat treatment, to facilitate the formation of a porous structure. The binder may be in liquid or solid form or a combination thereof, and may be composed of organic or inorganic components. A suitable liquid binder, such as ethylene or polyethylene glycol, may be used, although a solid binder of a wax or a combination of wax and other volatile components, which will vaporize at the heat-treatment temperature without leaving a residue, is preferred. The preferred binder is composed substantially or entirely of wax, with the remainder, if any, of an organic or hydrocarbon compound to control the malleability of the dental material. The term "wax," for purposes of the present invention, means any natural wax, mineral wax, or organic wax, or combination thereof. The concentration of the binder is preferably high enough to assure a void volume of at least twenty percent (20%). When the concentration of binder is at least twenty percent (20%) by volume, the relationship between void volume and binder is substantially one-to-one.

In addition to the metal particles and binder, the dental material should preferably contain a small amount of carbonaceous particles of preferably activated carbon. Activated carbon is a well-known, porous, carbonaceous material formed by heat-treating carbon or subjecting it to reaction with gases, sometimes adding chemicals, for example, zinc chloride, during or after carbonization, in order to increase its porosity. Its high porosity results in a very high surface area of many orders of magnitude larger than its untreated surface area. Activated carbon has a large absorption capacity to different gases. The carbonaceous particles from which activated carbon is formed may be of any conventional carbon material, including carbon black, coke flour, calcined lamp black flour, and the like. Suitable amounts of the activated carbon particles in the dental material of the present invention are from five-thousands of one percent (0.005%) of the weight of the dental composition, to about five percent (5%) of the weight of the dental composition, with 0.05 wt.% to 1.0 wt.% being preferred. Finely divided particles smaller than 250 millimicrons in average diameter is preferred. The carbon particles act as a reducing agent during the heat-treatment procedures and, substantially burn out upon exposure to air, leaving little or no residue. The increased surface area provided by activated carbon permits a smaller concentration to be used with much greater absorption capacity relative to inactivated carbon particles.

In accordance with the present invention, a filler material is melted into the voids of the heat-treated porous structure to solidify the structure for forming the final dental restoration. The porous metal structure may be reshaped, if desired, into its final configuration before the filler material is added. The filler material may be any suitable ceramic or metal composition, preferably a precious metal composition.

The filler material may also be formed of a matrix of particles mixed with a wax binder having a composition and concentration similar to the composition and concentration of the binder used to form the porous structure. A minimum binder concentration of at least about twenty percent (20%) by volume is preferred, and up to eighty-five percent (85%) by volume. Fifty percent (50%) or more of the overall weight of the filler composition is preferably of individual or alloyed particles, of any size, containing between 90% to 98.5% gold and between 1.5% to 8.5% silver, preferably 2% to 5%, with the remainder selected from the group of metals such as copper, zinc, aluminum, magnesium, gallium, indium, tin, or any of the platinum group metals and/or elements from the third or fourth groups of elements of the periodic table. The weight of the remainder should not exceed seven percent (7%) of the total weight. The other fifty percent (50%) of the filler composition may be composed entirely of gold, although other metals may be included, provided the silver content of the total filter composition is limited to no more than ten percent (10%) by weight, and the total of the other metals is also limited to ten percent (10%) by weight. The addition of metals, other than gold and silver, may be added to provide a melting gradient during melting of the filler material.

If wax is used as the binder, its composition is not critical, and any natural wax, mineral wax, organic wax, or synthetic wax composition may be used. The preferred wax is relatively soft and tacky, and should melt relatively cleanly, as should any other binder constituent, without leaving a significant residue. The vaporizing temperature of the binder must be below the melting temperature of the low-fusing temperature metal particles, and below the melting temperature for the filler material. Moreover, the high- and low-fusing temperature metal particles should combine with the binder and activated carbon particles to form a mixture with a uniform distribution of metal particles in the binder. Alternatively, the binder can be heated and the particles added and mixed, to form a uniform distribution of metal particles. The binder may include additives to control the malleability of the composition, and as a substitute for wax. The additives may be selected from elastomers, gums, synthetic rubbers, polysaccharides, and any organic or hydrocarbon compound similar to wax, such as paraffin oil. The additives should have a desirable vaporizing temperature at or below the heat-treatment temperature, and should not leave a residue upon heat treatment.

The high-fusing temperature metal component may be of a single metal or metal alloy, preferably of precious metals such as platinum and/or palladium, in any desired proportion relative to each other, from zero to one hundred percent, with or without other constituents such as gold, silver, copper, magnesium, aluminum, zinc, gallium, indium, and other metals or elements from the third, fourth, or fifth group of elements of the periodic table. Gold may be added to the high-fusing temperature metal component to increase the affinity of the high-fusing temperature metal component to the low-fusing temperature metal component, or to itself in the absence of the low-fusing component. In the latter instance, gold may represent the major constituent of the high-fusing metal component, and, depending on its concentration, will form a composition which may melt, or at least partially melt, at a temperature as low as 900–950° C. to permit the particles to join.

The concentration of the volatile binder in the dental material substantially controls the void volume of the porous structure after heat treatment, as well as the uniformity of the capillary network formed between the voids which, in turn, controls the absorption and accommodation of the filler material in the porous structure. The heat treatment must eliminate the binder, preferably without leaving a residue, and cause the low-fusing particles, if present, to melt to form a stable porous metal structure with a twenty (20%) to eighty percent (80%) void volume and a uniformly distributed void matrix. The void volume will substantially correspond in percent to the percent concentration of binder before heat treatment, provided it is above the minimum concentration of twenty percent (20%). The activated carbon is believed to reduce any oxygen which may be present during heat treatment into carbon dioxide, and protects the hot sponge from oxidizing in the presence of oxygen upon cooling.

In accordance with the preferred embodiment of the present invention, high- and low-fusing temperature metal particles are mixed with the carbon or activated carbon particles and binder to form a moldable base material. The base material may be compressed into a compacted strip or in any desired geometrical shape, having any thickness between twenty-five (25) microns and ten (10) millimicrons. The filler material may, likewise, be compacted into a strip or other geometry, for ease of application to the porous structure.

To form a coping from the base material, the base material is applied to the surface of a die by hand-molding, using pressure, with or without the use of an adhesive. A conventional adhesive may be used or an adhesive composed of a wax with a solvent and other adhesive agents, fluxes, etc. Hand-molding is done with the aid of a spatula or other hand instrument. The carving of the base metal-wax material into a preferred shape may be done on a model and then removed, or supported in any other fashion, for heat treatment. The heat treatment may be done in a furnace or under or over a flame. The usual heat-treatment temperature range for the base material is between 800° C. and 1200° C. The heat treatment of the filler material may also be done in a furnace or using a flame at a temperature generally below the heat-treatment temperature, substantially equal to, or slightly above the first heat-treatment temperature. In accordance with an alternative embodiment of the present invention, finely divided particles of activated carbon are mixed with adhesive and applied over the die before the moldable base material is applied to the die. This latter procedure may be practiced using a moldable dental base material composed of a mixture of high- and low-fusing temperature metal particles and binder with or without particles of carbon or activated carbon. However, the incorporation of carbon particles in the base material is preferred, even if carbon particles are added to the adhesive. When the moldable dental base material does not contain particles of carbon or activated carbon, the proportion of the activated carbon particles in the adhesive to the weight of the metal applied over it for forming a coping should correspond to that used when mixed in the base metal, as earlier discussed, for forming the preferred base composition.

During the heat treatment, the binder burns out to form the spongy structure. Filler material is then added to the porous structure and heat treated to form a dense solid coping. Once the metal coping is formed, a conventional porcelain or acrylic veneer may be applied thereover to form a conventional ceramic-to-metal restoration.

When the high-fusing particles are substantially all of irregular geometry and preferably of minimal thickness and/or orientation, as will be explained hereafter, the moldable dental composition of the present invention may be limited to only high-fusing metal particles, that is, the low-fusing metal particles may be excluded from the composition, leaving only high-fusing metal particles, a binder, and carbon or activated carbon particles to form the moldable base material. However, in general, it is preferable, but not essential, for the composition to include at least a minor or nominal percentage of low-fusing metal particles to enhance the wetting of the high-fusing particles during heat treatment. The particles of low-fusing temperature metal are composed preferably of gold or a gold alloy, with gold as the major constituent. The preference for gold as the major constituent of the low-fusing component is based on its known characteristics of workability, biocompatibility, non-oxidizing properties, and color. The low-fusing metal particles must, of course, have a melting temperature below that of the high-fusing metal particles.

The shape of the high-fusing metal particles in the moldable dental material has been found to be important to maintain dimensional control over the voids formed between the high-fusing particles during heat treatment. Irregular shape particles, in the form of flakes,—that is, platelets which are very thin—function best. The size and dimensions of the irregular, flake-like particles play an important function. The very thin platelets of high-fusing particles interleave one another to provide sufficient mechanical integrity to form a porous structure during heat treatment without the presence of low-fusing particles and, surprisingly, will retain its structure after heat treatment with minimal shrinkage. It is postulated that even without low-fusing particles, the heat-treatment operation forms localized, autogenous joints which maintain the structural integrity of the porous structure after heat treatment. However, the porous structure formed with the use of low-fusing particles as part of the composition is still preferred.

It is preferred that at least fifty percent (50%) of the high-fusing metal particles have a thin, cross-sectional, average thickness of less than about 1.5 microns. The following test, in combination with the examples given below, should be employed to determine if fifty percent (50%) of the high-fusing particles meet this 1.5 micron thickness limitation: (a) the surface area of the largest two-dimensional surface (or its "projected image") for each of the high-fusing particles should be measured, (b) the total surface area of all of the high-fusing particles should be calculated, and (c) the cumulative surface area of the high-fusing particles below 1.5 microns in average thickness should then be divided by the computed total surface area. The surface area calculation is a simple two-dimensional measurement of the area circumscribing the flat, planar surface containing the largest two-dimensional image of each particle. If the planar geometry of the particle were rectangular, the surface area would simply be the length times the width. As an illustration, assume a high-fusing particle flake geometry of $5\mu(\text{long}) \times 10\mu(\text{wide}) \times 3$ microns thick. The largest two-dimensional surface area is $5\mu \times 10\mu$. For a second illustration, assume a geometry of $20\mu(\text{long}) \times 5\mu(\text{wide}) \times 1\mu(\text{thick})$. Again, the largest two-dimensional surface area is $20\mu \times 5\mu$. As a third example, assume a flake geometry of a ball having a diameter of 20 microns. A two-dimensional projected image would be a circle having a surface area of $\pi r^2$ or $\pi 100$. The taking of a "projected image" of the largest two-dimensional surface maybe necessary based on undulations and irregularities in the flake surfaces which would otherwise complicate the surface area calculation. The cumulative total of the surface area for all of the particles is preferably determined by statistical analysis. There are commercial analytical instruments and techniques available which may be used for computing the surface area of the particles. Preferably, most of the particles will have a very thin cross-sectional thickness of less than about 1.5 microns. However, since it is possible to break larger particles into many smaller particles, it is necessary to make a surface area measurement to determine if at least fifty percent (50%) of the total population of the high-fusing particles in the composition are of proper thickness.

As explained above, by appropriate selection of the geometry and size of high-fusing particles, the low-fusing particles may be entirely eliminated from the composition. A composition without low-fusing particles may be desirable for forming the abutments in dental bridgework. However, the inclusion of low-fusing particles is generally preferred and the best results are achieved using a mixture of both high- and low-fusing particles in a wax binder and carbon particles, with the high-fusing particles having the desired geometry and size. When using a mixture of metal particles, the relative volume percent of the low-fusing metal particles in the composition should lie in a range of from about forty percent (40%) to about sixty-five percent (65%) for most applications, and preferably between forty-two percent (42%) and fifty-five percent (55%) by volume. In general, if the volume percent of the high-fusing component in the composition is too large, particularly for a high-fusing component of high melting temperature, there may not be adequate wetting between the high-fusing particles during heat treatment. If the volume percent of the high-fusing component is too small, too much wetting will occur and the structure will collapse, that is, become too dense. As the average thickness of the high-fusing particles in the total composition decreases to below 1.5 microns, the volume percent of the low-fusing component within the above range may increase, particularly for thicknesses below 0.5 microns.

In general, the longest dimension of the high-fusing metal particle should not exceed an average of preferably about eighty (80) microns, and should preferably range from over two (2) to fifty (50) microns, with the average shortest dimension in a range of, preferably, between one (1) and twenty-five (25) microns in length, although the absolute values of these dimensions are not particularly significant. The high-fusing particles may be longer or equal in size to the low-fusing particles (with the low-fusing particles preferably measured by its diameter since the low-fusing particles are generally spherical).

When the high-fusing metal particles possess a flake-like geometry and are very thin, they overlap to form a lattice network of particles. This assures adequate strength even when the composition is thinned down near the dental margin without flaking. The thin flakes also assure a compact, open-pore structure of uniform porosity, which also provides a greater reliability of dimensional control over the voids in the heat-treated structure. The strength of the heat-treated structure is improved, however, when the high-fusing particles are not randomly oriented in the wax binder. Preferably at least thirty percent (30%) of the high-fusing particles should be unidirectionally oriented in parallel to one another to form laminations in a direction parallel to the surface of the material, that is, parallel to the longitudinal axis of the dental material. With this preferred orientation of high-fusing flakes of thin cross-sectional thickness, the low-fusing component may be omitted entirely or of low concentration. For this special case, the integrity of the heat-treated structure is dependent primarily upon the overlapping layered formation of the high-fusing particles.

What is claimed:

1. A moldable dental composition comprising high-fusing temperature metal particles having a melting temperature above the preselected temperature at which said dental composition is to be heat treated, with said particles having an irregular non-spherical geometry of which at least 50% have a cross-sectional average thickness of less than 1.5 microns, at least about 20% and up to 85% by volume of a volatile binder and carbonaceous particles in a concentration above at least 0.005 wt. % of the dental composition.

2. A moldable dental composition, as defined in claim 1, wherein said carbonaceous particles are particles of activated carbon.

3. A moldable dental composition as defined in claim 2, wherein said composition further comprises low-fusing temperature metal particles having a melting temperature below the melting temperature of the high fusing temperature metal particles and equal to or below the temperature at which said dental composition is to be heat treated.

4. A moldable dental composition, as defined in claim 3, wherein the concentration of said particles of activated carbon is between 0.05 wt. % and 5.0 wt. % of the dental composition.

5. A moldable dental composition, as defined in claim 4, wherein said activated carbon is in a range between 0.05 wt. % and 1.0 wt. % of the dental composition.

6. A moldable dental composition as defined in claim 5 wherein at least 30% of the high fusing temperature metal particles are unidirectionally oriented so as to form a layered structure upon heat treatment.

7. A moldable dental composition as defined in claim 4 further comprising a filler material for densifying the porous metal structure formed upon heat treatment of said dental composition.

8. A moldable dental composition, as defined in claim 7, wherein said filler material comprises gold.

9. A moldable dental composition as defined in claim 8 wherein said filler material further comprises wax in a concentration of at least about thirty percent by volume of said filler material.

10. A moldable dental composition as defined in claim 7 wherein said filler material comprises an alloy of at least fifty percent gold by weight and a metal selected from the group consisting of silver, copper, zinc, aluminum, magnesium, gallium, indium, the platinum group metals and elements from the third or fourth groups of elements of the periodic table of elements.

11. A moldable dental composition as defined in claim 3, further comprising a flux.

* * * * *